United States Patent
Prasad et al.

(10) Patent No.: US 12,406,099 B2
(45) Date of Patent: Sep. 2, 2025

(54) METHOD FOR SECURELY STORING AND RETRIEVING MEDICAL DATA

(71) Applicants: Siemens Healthcare GmbH, Erlangen (DE); Biosense Webster (Israel) Ltd., Yokneam (IL)

(72) Inventors: Srikrishna Prasad, Erlangen (DE); Michael Kelm, Erlangen (DE); Ute Rosenbaum, Kempten (DE); Daniel Nottebrock, Nuremberg (DE); Anthony Jay, Erlangen (DE); Manuel Sujith, Erlangen (DE); Srividya Tirunellai Rajamani, Erlangen (DE); Amatzia Tov, Kibbutz Reshafim (IL); Matityahu Amit, Zur-Yigal (IL)

(73) Assignee: Siemens Healthineers AG, Erlangen (DE)

( * ) Notice: Subject to any disclaimer, the term of this patent is extended or adjusted under 35 U.S.C. 154(b) by 364 days.

(21) Appl. No.: 17/470,369

(22) Filed: Sep. 9, 2021

(65) Prior Publication Data

US 2022/0075903 A1 Mar. 10, 2022

(30) Foreign Application Priority Data

Sep. 10, 2020 (EP) .................................. 20195563

(51) Int. Cl.
*G06F 21/78* (2013.01)
*G06F 21/60* (2013.01)
(Continued)

(52) U.S. Cl.
CPC ............ *G06F 21/78* (2013.01); *G06F 21/602* (2013.01); *G16H 10/60* (2018.01); *G16H 30/20* (2018.01); *H04L 9/0825* (2013.01)

(58) Field of Classification Search
CPC .... G06F 21/78; G06F 21/602; G06F 21/6254; G06F 21/57; G06F 21/6245; G16H 10/60;
(Continued)

(56) References Cited

U.S. PATENT DOCUMENTS

| | | | |
|---|---|---|---|
| 2005/0165623 A1* | 7/2005 | Landi | H04L 9/083 705/2 |
| 2011/0191245 A1* | 8/2011 | Ricciardi | H04L 9/3226 705/51 |

(Continued)

FOREIGN PATENT DOCUMENTS

| | | |
|---|---|---|
| CN | 102414688 A | 4/2012 |
| CN | 104680076 A | 6/2015 |

(Continued)

OTHER PUBLICATIONS

European Search report corresponding to European Patent Application No. EP 20 19 5563 (8 pages).

(Continued)

*Primary Examiner* — Harunur Rashid
(74) *Attorney, Agent, or Firm* — Maginot, Moore & Beck LLP

(57) ABSTRACT

A gateway and a method are provided for securely storing (and/or securely retrieving) medical data the method for storing comprising at least steps of:
obtaining, in a secure environment, medical data which include patient property data as well as patient identifier data wherein the patient identifier data indicate at least one patient to which the patient property data correspond;
generating, in the secure environment de identified medical data by replacing the patient identifier data in the medical data with non-patient-identifying coded identifiers;

(Continued)

generating, in the secure environment, a re-identifying database indicating correspondences between the non-patient-identifying coded identifiers and the patient identifier data;

generating an encrypted re-identifying database by applying, in the secure environment, at least one symmetric and/or asymmetric encryption method to the re-identifying database;

storing the encrypted re-identifying database and the de-identified medical data on a cloud storage outside of the secure environment.

13 Claims, 4 Drawing Sheets

(51) Int. Cl.
  *G16H 10/60*   (2018.01)
  *G16H 30/20*   (2018.01)
  *H04L 9/08*   (2006.01)

(58) Field of Classification Search
  CPC ...... G16H 30/20; G16H 15/00; H04L 9/0825; H04L 2209/88; H04L 9/0894; H04L 2209/42; H04L 63/0421
  See application file for complete search history.

(56) References Cited

U.S. PATENT DOCUMENTS

| | | |
|---|---|---|
| 2013/0208966 A1 | 8/2013 | Zhao |
| 2014/0136237 A1* | 5/2014 | Anderson .............. G16H 10/60 705/3 |
| 2016/0277374 A1* | 9/2016 | Reid ................... H04L 63/0435 |
| 2017/0076109 A1* | 3/2017 | Kaditz ................... G16H 40/20 |
| 2019/0081783 A1* | 3/2019 | Bohli ...................... G06F 3/064 |
| 2019/0205566 A1 | 7/2019 | Shelton, IV et al. |
| 2020/0143084 A1* | 5/2020 | Rosenberg ............. G16H 10/60 |

FOREIGN PATENT DOCUMENTS

| | | |
|---|---|---|
| CN | 111602205 A | 8/2020 |
| JP | 2007-20065 A | 1/2007 |
| JP | 2014-66831 A | 4/2014 |
| JP | 2014-519655 A | 8/2014 |
| JP | 2015-512100 A | 4/2015 |
| WO | 2013/123085 A1 | 8/2013 |

OTHER PUBLICATIONS

Office Action for corresponding CN application No. CN202111057472.7, mailed Oct. 30, 2024 (8 pages).

* cited by examiner

METHOD FOR SECURELY STORING AND RETRIEVING MEDICAL DATA

PRIORITY CLAIM

This application claims priority to European Application No. EP 20195563.0, filed on Sep. 10, 2020. The entire contents of the above-mentioned European patent are incorporated herein by reference as part of the disclosure of this U.S. application.

FIELD OF THE INVENTION

The present invention pertains to a method for securely storing data, as well as a corresponding system, computer program, data storage medium and data stream. One important application is the backup of sensitive data.

Although applicable for any kind of data, the present invention and the corresponding underlying problems will be explained in further detail in conjunction with medical data.

BACKGROUND OF THE INVENTION

Increasing amounts of digital data in the healthcare sector open new possibilities but also pose new challenges, in particular with respect to data privacy and data security. Currently, major legal provisions in this respect are, for example, the US-American Health Insurance Portability and Accountability Act (HIPAA) or the European General Data Protection Regulation (GDPR).

On the other side, it is desired that tenants in the medical domain, such as hospitals or research institutions, are able to provide data push/pull systems or services, in particular with respect to cloud applications. The above mentioned considerations usually have the effect that medical data is either pseudonymized or encrypted even if data is accessed inside a hospital network. This hinders the management of workflows as patient data cannot be re-identified and hence data sets cannot be (re-)associated with a specific patient.

Another challenge is that the medical data must be stored safely so that regular backups must be made. In principle, cloud storage solutions are well suited for backup applications, as they are usually hosted remotely from tenant premises and are thus not susceptible to the same incidents that may cause data deletion or corruption at the tenant's premises itself. At the same time, data privacy must be maintained also for the backups. Local backups, i.e. in the (presumably secure) environment of the tenant are possible, although they are not only susceptible to whatever may befall the original data (e.g., natural disasters like flood or fire) but also represent a significant cost factor in hardware and maintenance.

SUMMARY OF THE INVENTION

According to the foregoing, it is an object of the present invention to provide a method for securely storing medical data, as well as a corresponding system, computer program, data storage medium and data stream.

This object is solved at least by the features according to the independent claims of the present invention. Additional advantageous features and embodiments are described in the dependent claims and the specification.

According to a first aspect of the present invention, a computer-implemented method for securely storing medical data, MD, is provided, the method comprising at least steps of:

obtaining, in a secure environment, medical data which include patient property data, PPD, as well as patient identifier data, PID, wherein the patient identifier data, PID, indicate at least one patient to which the patient property data, PPD, correspond;

generating, in the secure environment, de-identified medical data, DIMD, by replacing the patient identifier data, PID, in the medical data, MD, with non-patient-identifying coded identifiers, NPICI;

generating, in the secure environment, a re-identifying database, RIDB, indicating correspondences (preferably one-on-one correspondences) between the non-patient-identifying coded identifiers, NPICI, and the patient identifier data, PID;

generating an encrypted re-identifying database, eRIDB, by applying, in the secure environment, at least one symmetric and/or asymmetric encryption method to the re-identifying database, RIDB;

storing the encrypted re-identifying database, eRIDB, and the de-identified medical data, DMID, on a cloud storage, CS, outside of the secure environment, SE.

The secure environment, SE, may in particular be an intranet associated with a particular tenant, such as a hospital's internal network. The secure environment, SE, may also be defined such that for data queries within the secure environment, SE, it is allowed (or even the default) that patent property data, PPD, are displayed together with the patent identifier data, PID. The secure environment, SE, may also be designated as a trusted environment, TE, since it is, in the present context, by definition that this environment is secure. The present disclosure does not pertain to methods for rendering the trusted environment secure. It is instead assumed that all necessary precautions have been taken.

In the present context, patient identifier data, PID, are data which allow identifying a particular patient, such as data comprising a clear name of the patient, a birthday or age of the patient, the sex of the patient, a social security number of the patient, a healthcare provider ID of the patient, a passport number of the patient and/or the like.

By contrast, patient property data, PPD, shall be understood in the present context to be data pertaining to particular properties, in particular medical details, of a patient, however, without indicating (or allowing deduction of) the identity of the patient itself. Thus, patient property data, PPD, may comprise such items as blood test results, previous diagnoses, the medical history, currently known medical symptoms and/or conditions, health insurance data, medical images related to the patient (e.g. X-ray images, computed tomography images or magnetic resonance images) and/or the like of the patient or patients. The patient property data, PPD, may also be designated as patient medical records, PMR.

The medical data preferably comprise patient property data, PPD, for a plurality of patients, wherein the patients to which the respective patient property data, PPD, belong, are identified by the patient identifier data, PID, of the medical data.

Thus, replacing the patient information data, PID, with the non-patient-identifying coded identifier, NPICI, means that, advantageously, the de-identified medical data, DIMD, can be used for studies, for diagnostic purposes, for the training of artificial intelligence entities, for statistics and so on without any information about to whom the individual patient property data, PPD, belong to. In other words, the identities of the patients are protected while their data may be securely used for research and the like, or for processing outside of the secure environment, SE.

On the other hand, the existence of the re-identifying database, RIDB, and the one-to-one correspondences between the respective patient identifier data, PID, and the non-patient-identifying coded identifiers, NPICI, guarantees that a person with suitable clearance (e.g. a physician, a hospital administrator etc.) can easily re-identify the de-identified medical data, DIMD, i.e. can re-associate the patient property data, PPD, with each corresponding patient identifier data, PID, or in other words: with each patient.

In this way, advantageously a full backup of the medical data, MD, is provided by the presence in the cloud storage, CS, of the de-identified medical data, DIMD, and of the encrypted re-identifying database, eRIDB, since with these two pieces together (given the clearance to decrypt the encrypted re-identifying database, eRIDB) the entire medical data, MD, can be restored.

The de-identified medical data, DIMD, may be stored on the cloud storage, CS, as it is, or it may be stored in an encrypted state, as encrypted de-identified medical data, eDIMD. In the latter case, the same encryption type and/or encryption key or keys as for the encrypted re-identifying database, eRIDB, may be used, or a different encryption type and/or encryption key or keys may be used.

On the other hand, because of the de-identification, the de-identified medical data DIMD may be stored in the cloud storage, CS, in an unencrypted state (in plain text, designated as pDIMD) so that it can be provided to third parties for further processing, e.g. for the training of artificial intelligence entities (e.g. machine learning, artificial neural networks etc.), or for statistics about characteristics of a certain patient cohort. Of course, access to the cloud storage itself will usually be restricted by password or the like so that only users authorized users may receive the de-identified medical data, DIMD, for example after a payment, in connection to a smart contract and/or the like.

The re-identifying database, RIDB, will, however, only be stored in its encrypted state (eRIDB) on the cloud storage, CS. The reason is that no entity outside of the secure environment, SE, is supposed to be in possession of both the de-identified medical data, DIMD, and the re-identifying database, RIDB, since this would amount to possession of or access to the complete medical data, MD.

Advantageously, the present method allows, since the re-identifying database, RIDB, is available within the secure environment, SE, that authorized personnel, authorized applications/software etc. to access the medical data, MD, including the patient identifier data, PID. This greatly facilitates diagnosis, treatment, monitoring and so on of patients on hospital premises (corresponding to the secure environment, SE).

In some advantageous embodiments, refinements, or variants of embodiments, at least an asymmetric encryption method is applied when generating the encrypted re-identifying database, eRIDB, the asymmetric encryption method being based on a private key, PRK, and a public key, PUK, wherein a public key, PUK, of the asymmetric encryption method is used for the asymmetric encryption and wherein a private key, PRK, for a corresponding decryption remains in the secure environment, SE. The application of different types of encryption increases the difficulty for attempted decryption by unauthorized entities. Preferably, both at least one symmetric and at least one asymmetric encryption method are applied when generating the encrypted re-identifying database, eRIDB.

In some advantageous embodiments, refinements, or variants of embodiments, the public key, PUK, and/or the private key, PRK, are stored in a domain of the secure environment SE in a respective encrypted state, ePUK/ePRK. Storage in the domain of the secure environment SE may be understood to mean storage within the secure environment, SE, itself, for example on the premises of a hospital which implements the secure environment, SE.

Storage in the domain of the secure environment SE may also be understood to mean that a person with clearance within the secure environment, SE, such as a hospital administrator or a physician has custody of the encrypted public and/or encrypted private key, ePUK/ePRK (e.g., by having custody of a storage medium storing the encrypted public and/or encrypted private key, ePUK/ePRK). The corresponding encrypted states, ePUK/ePRK may advantageously result from encrypting the public key, PUK, or the private key, PRK, respectively, using an secure-environment-specific token, SEST. In this way, the keys are also protected against unauthorized use within the secure environment, SE, and therefore also against attempts to gain access to the keys by gaining physical access to premises corresponding to, or implementing, the secure environment, SE.

In some advantageous embodiments, refinements, or variants of embodiments, the secure-environment-specific token, SEST, is based on at least one of:
   an identifier token (e.g. a serial number) of the secure environment, SE;
   an identifier token of at least one device in the secure environment, SE (for example a gateway, a medical data source such as a medical imaging scanner);
   an identifier token of at least one software application used within the secure environment, SE (such as an analysis program);
   an RFID code of a dongle owned by an administrator; and/or
   a version number of data to be encrypted using the public key, PUK.

In some advantageous embodiments, refinements, or variants of embodiments, the encrypted re-identifying database, eRIDB, (and/or other data to be backed up, e.g. the de-identified medical data, DIMD) is/are additionally stored in a device in the secure environment, SE, for example in the gateway, in a PACS, in a medical imaging device and/or the like. This provides additional redundancy and reduced latency. Moreover, currently unused non-transitory memory within the secure environment may be used instead of occupying additional non-transitory memory on the cloud storage. The retrieval of the files backed up within devices in the secure environment, SE, may be performed in analogy to what is described with respect to retrieval from the cloud storage, CS.

The storing in a device of the secure environment, SE, may be performed in the DICOM format, i.e. by encapsulating the data to be stored as one or more DICOM files. Whenever DICOM is mentioned herein, it shall be understood that this refers to the "Digital Imaging and Communications in Medicine" (DICOM) standard, for example according to the current DICOM PS3.1 2020c standard (or any later or earlier version of said standard).

In some advantageous embodiments, refinements, or variants of embodiments, the encrypted re-identifying database, eRIDB, is generated as consisting of, or processed to consist of, a plurality of chunks (i.e. individual data containers or fragments) which are stored on the cloud storage, CS. Storing (or: uploading) of individual chunks on (or to) the cloud storage, CS, is less error-prone than uploading comparatively large single-file databases. Moreover, as will be described in the following, the presence of a large number of chunks on the cloud storage, CS, provides additional security against unauthorized access attempts. In the present context, each chunk may be understood to be one of a plurality of parts of the encrypted re-identifying database, eRIDB, or may be one of a plurality of parts of the plain text re-identifying databased, pRIDB, wherein said parts (i.e. the chunks) are then individually encrypted to form together the encrypted re-identifying database, eRIDB.

Specifically, in some advantageous embodiments, refinements, or variants of embodiments, chunks belonging to at least two different versions of the re-identifying database, RIDB, may be stored in an encrypted state on the cloud storage (CS). Thus, a history of the re-identifying database, RIDB, can also be backed up.

Preferably, the chunks do not contain any plain text information about a version to which they belong. They may, however, be labelled with a coded identifier such as a hash value which is used to uniquely identify each chunk. For example, the hash value may be a hash of each chunk (and, optionally, its version number) generated using a secure hash algorithm, e.g. SHA-1, SHA-2, SHA-3 and/or the like. The coded identifier may be used, for example, as the name of the chunk as it is stored on the cloud storage, CS.

The method in this variant advantageously also comprises a step of generating a version correspondence list, VCL, which indicates (at least) which chunks belong to which version. The version correspondence list, VCL, may to this end indicate correspondences (preferably one-on-one correspondences) between the coded identifier of each chunk on the one side and the version number (and optionally additional details) of the chunk on the other side. Thus, for efficient decrypting, the version correspondence list becomes increasingly important with an increasing number of versions of the same object (e.g. encrypted re-identifying database, eRIDB) on the cloud storage, CS. This in turn means that the challenges for an unauthorized attacker increase as well.

In some advantageous embodiments, refinements, or variants of embodiments, the method comprises further steps of encrypting the version correspondence list, VCL, to obtain an encrypted version correspondence list, eVCL. Since decryption of the encrypted re-identifying database, eRIDB, realized as a number of chunks is exceedingly difficult without the version correspondence list, VCL, efficiently backing up the re-identifying database, RIDB, thus means that also the version correspondence list, VCL, should be protected by encryption, and preferably also similarly backed up.

For example, the encrypted version correspondence list, eVCL, may be stored on the cloud storage, CS, as well. The encryption used for the version correspondence list, VCL, may use the same encryption protocols and/or encryption keys as the encryption of the re-identifying database, RIDB, or may use different protocols and/or keys.

In some advantageous embodiments, refinements, or variants of embodiments, the method includes a step of generating encrypted de-identified medical data, eDIMD. The step of storing the de-identified medical data, DIMD, on the cloud storage, CS, may comprise, or consist of, storing the encrypted de-identified medical data, eDIMD, on the cloud storage, CS. Additionally or alternatively, storing the de-identified medical data, DIMD, on the cloud storage, CS, may comprise, or consist of, storing plain text de-identified medical data, pDIMD, on the cloud storage, CS.

Since the plain text de-identified medical data, pDIMD, do not contain any patient identifier data, PID, it is according to many data protection rules systems allowable to store them in an unencrypted, i.e. plain text, state on the cloud storage, CS. This has the additional advantage that third parties or entities outside of the secure environment may be granted access to the plain text de-identified medical data, pDIMD, and may further process them. For example, the plain text de-identified medical data, pDIMD, may be used for training an artificial intelligence entity such as an artificial neural network, or for another machine learning application.

In some advantageous embodiments, refinements, or variants of embodiments, the method may be designated as a method for securely storing and securely retrieving medical data. The method may comprise steps of:
  retrieving (for example: downloading) the de-identified medical data, DIMD, from the cloud storage, CS;
  retrieving (for example: downloading) the encrypted re-identifying database, eRIDB, from the cloud storage, CS;
  decrypting, in the secure environment, SE, the encrypted re-identifying database, eRIDB, in order to obtain the plain text re-identifying database, pRIDB;
  regenerating the medical data, MD, from the de-identified medical data, DMID, by replacing, or associating, the non-patient-identifying coded identifiers, NPICI, in the de-identified medical data, DIMD, with the corresponding patient identifier data, PID, based on the re-identifying database, RIDB. These steps (as also any of the other steps of the method) may be advantageously performed by a gateway of the secure environment.

In some advantageous embodiments, refinements, or variants of embodiments, the method further comprises a step of providing, or making available, the de-identified medical data, DIMD, from the cloud storage, CS, to a processing entity outside of the secure environment, SE. For example, the method may further comprise training, by the processing entity, an artificial intelligence entity based on the de-identified medical data, DIMD.

According to a second aspect, the present invention also provides a gateway for use in a secure environment.

Specifically, the gateway may comprise:
  an input module configured to obtain medical data, MD, which include patient property data, PPD, as well as patient identifier data, PID, wherein the patient identifier data, PID, indicate at least one patient to which the patient property data, PPD, correspond;
  a de-identifying module configured to generate de-identified medical data, DIMD, by replacing the patient identifier data, PID, in the medical data, MD, with non-patient-identifying coded identifiers, NPICI;
  a database generating module configured to generate a re-identifying database, RIDB, indicating (preferably one-on-one) correspondences between the non-patient-identifying coded identifiers, NPICI, and the patent identifier data, PID;
  an encryption module configured to generate an encrypted re-identifying database, eRIDB, by applying at least one symmetric and/or asymmetric encryption method to the re-identifying database, RIDB;
  a communication module configured to transmit the encrypted re-identifying database, eRIDB, and the de-identified medical data, DMID to be stored on a cloud storage, CS, outside of (or: separate from) the secure environment, SE.

Whenever any modules are mentioned herein, it shall be understood that this may refer to modules realized as hardware and/or as software. The modules are mentioned and described as a way of facilitating understanding, and it will be clear that all functions of all modules may be realized by one and the same body of computer program instructions (or: computer code). Moreover, the functions of any or all modules may overlap, and some modules may be integrated into other modules, without departing from the present disclosure. Any or all modules might comprise or consist of at least one of a microprocessor, a CPU (acronym for "central processing unit"), a GPU (acronym for "graphical processing unit"), a field programmable gate array (an acronym is "FPGA") or an ASIC (acronym for "application-specific integrated circuit").

According to embodiments of the second aspect of the present invention, the gateway may in particular be configured to perform the method according to any embodiment of the first aspect of the present invention. Thus, the gateway may be modified or adapted to any advantageous variant, refinement, or embodiment that is described herein for the method according to the first aspect.

According to a third aspect of the present invention, a system is provided which includes a gateway according to an embodiment of the second aspect of the present invention as well as a cloud storage, CS, which are operatively linked or linkable to one another, so that the gateway may store data, preferably encrypted data such as the encrypted re-identifying database, eRIDB, encrypted version correspondence list, eVCL, and/or the like on the cloud storage, CS, and optionally retrieve the stored data again from the cloud storage, CS. Thus, one function of the system is to provide a cloud-based backup for the medical data obtained in or by the gateway. The system may in particular be configured to perform the method according to any embodiment of the first aspect of the present invention.

According to a fourth aspect, the invention also provides a method for securely retrieving medical data. The method may comprise steps of:

retrieving (for example: downloading) de-identified medical data, DIMD, from a cloud storage, CS, wherein the de-identified medical data, DIMD, comprise patient property data, PPD, as well as non-patient-identifying coded identifiers, NPICI;

retrieving (for example: downloading) an encrypted re-identifying database, eRIDB, from the cloud storage, CS;

decrypting, in a secure environment, SE, the encrypted re-identifying database, eRIDB, in order to obtain a plain text re-identifying database, pRIDB, which indicates correspondences (preferably one-on-one correspondences) between the non-patient-identifying coded identifiers, NPICI, and patient identifier data, PID, which indicate at least one patient to which the patient property data, PPD, correspond;

regenerating (plain text) medical data, MD, from the de-identified medical data, DIMD, by replacing, or associating, the non-patient-identifying coded identifiers, NPICI, in the de-identified medical data, DIMD, with the corresponding patient identifier data, PID, based on the (plain text) re-identifying database, RIDB.

This method may be performed by another entity as the method according to embodiments of the first aspect. For example, when a hospital opens a new branch hospital and the medical data stored at the hospital are to be copied to the new branch hospital, the original hospital may use the method according to embodiments of the first aspect to securely upload (store) the medical data, and the new branch hospital may use the method according to embodiments of the fourth aspect in order to securely download (retrieve) the medical data.

These steps (as also any of the other steps of the method) may be advantageously performed by a gateway of the secure environment.

According to a fifth aspect, the present invention also provides a gateway configured to perform the method according to any embodiment of the fourth aspect of the present invention, specifically, a gateway for use in a secure environment which comprises:

a communication module configured to:
retrieve (for example: download) de-identified medical data, DIMD, from a cloud storage, CS, wherein the de-identified medical data, DIMD, comprise patient property data, PPD, as well as non-patient-identifying coded identifiers, NPICI;
retrieve (for example: download) an encrypted re-identifying database, eRIDB, from the cloud storage, CS;

a decryption module configured to decrypt at least the encrypted re-identifying database eRIDB;

a re-identifying module configured to re-generate (plain text) medical data, MD, from the de-identified medical data, DIMD, by replacing, or associating, the non-patient-identifying coded identifiers, NPICI, in the de-identified medical data, DIMD, with the corresponding patient identifier data, PID, based on the (plain text) re-identifying database, RIDB.

According to a sixth aspect of the present invention, a system is provided which includes a gateway according to an embodiment of the fifth aspect of the present invention as well as a cloud storage, CS, which are operatively linked or linkable to one another, so that the gateway may retrieve data, preferably encrypted data such as the encrypted re-identifying database, eRIDB, encrypted version correspondence list, eVCL, and/or the like from the cloud storage, CS. Thus, one function of the system is to employ a cloud-based backup. The system may in particular be configured to perform the method according to any embodiment of the fourth aspect of the present invention.

According to a seventh aspect, the invention provides a computer program product comprising executable program instructions configured to, when executed, perform the method according to any embodiment of the first aspect and/or the method according to any embodiment of the fourth aspect.

According to an eighth aspect, the invention provides a non-transient computer-readable data storage medium comprising executable program instructions configured to, when executed, perform the method according to any embodiment of the first aspect and/or the method according to any embodiment of the fourth aspect.

The non-transient computer-readable data storage medium may comprise, or consist of, any type of computer memory, in particular semiconductor memory such as a solid-state memory. The data storage medium may also comprise, or consist of, a CD, a DVD, a Blu-Ray-Disc, an USB memory stick, a memory card (e.g. an SD card) or the like.

According to a ninth aspect, the invention provides a data stream representing, or configured to generate, executable program instructions configured to, when executed, perform the method according to any embodiment of the first aspect and/or the method according to any embodiment of the fourth aspect.

Additional advantageous variants, refinements, embodiments and aspects of the invention will become more obvious in connection with the following description with reference to the drawings.

BRIEF DESCRIPTION OF THE DRAWINGS

The invention will be explained in yet greater detail with reference to exemplary embodiments depicted in the drawings as appended.

The accompanying drawings are included to provide a further understanding of the present invention and are incorporated in and constitute a part of the specification. The drawings illustrate the embodiments of the present invention and together with the description serve to illustrate the principles of the invention. Other embodiments of the present invention and many of the intended advantages of the present invention will be readily appreciated as they become better understood by reference to the following detailed description. Like reference numerals designate corresponding similar parts.

Figure 1:
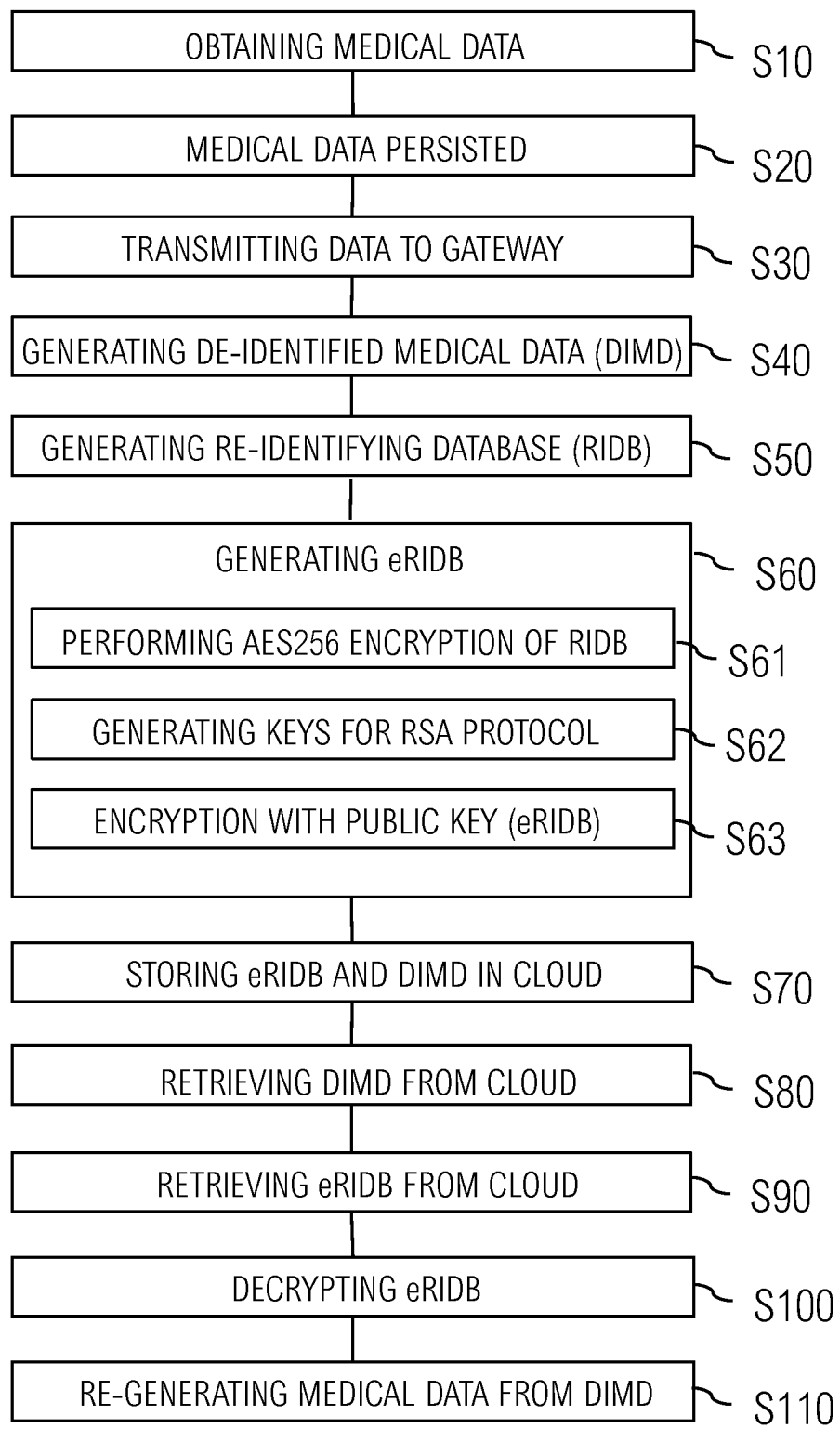

The numbering of method steps is intended to facilitate understanding and should not be construed, unless explicitly stated otherwise, or implicitly clear, to mean that the designated steps have to be performed according to the numbering of their reference signs. In particular, several or even all of the method steps may be performed simultaneously, in an overlapping way or sequentially.

Figure 2:
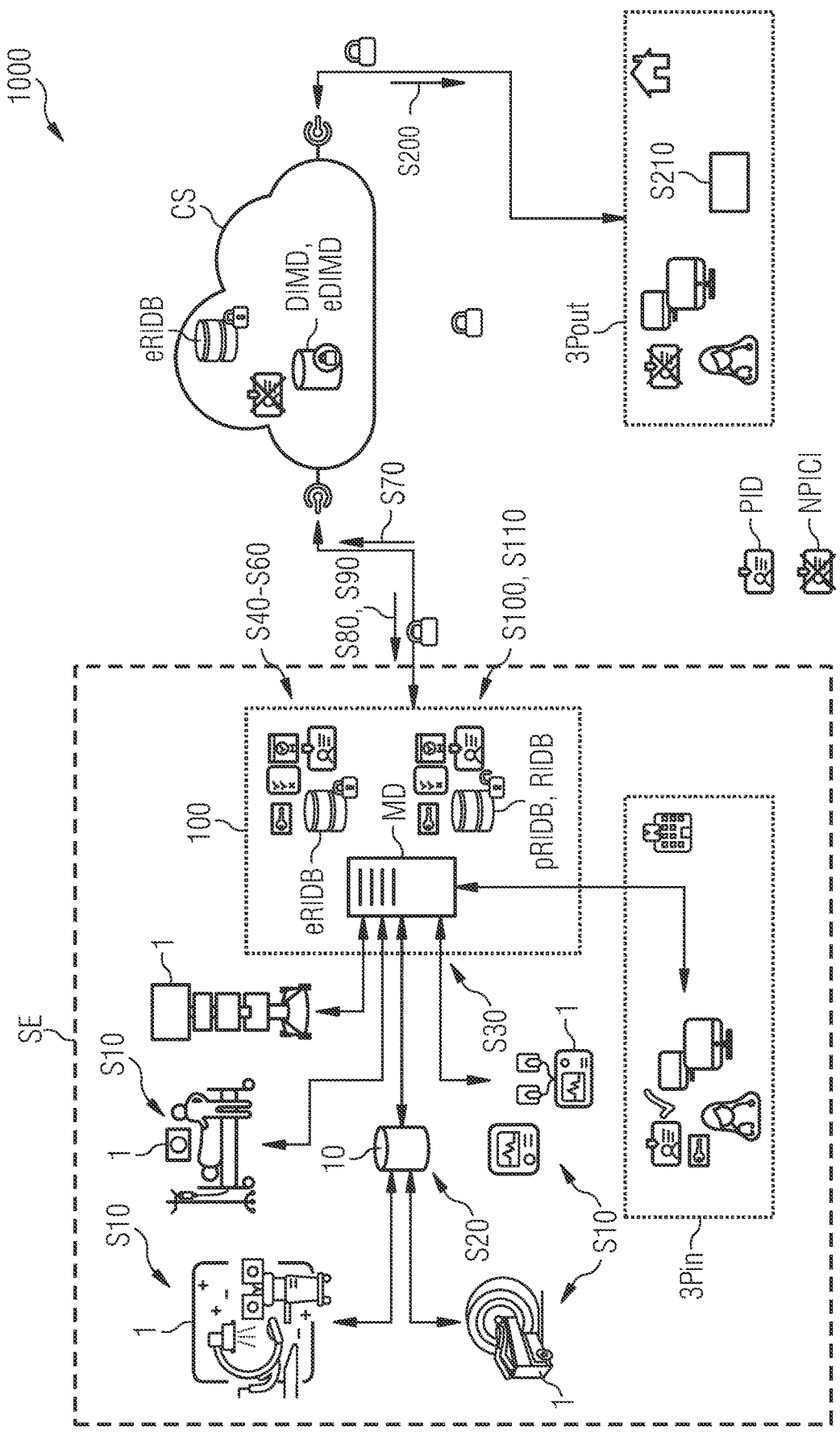
Figure 3:
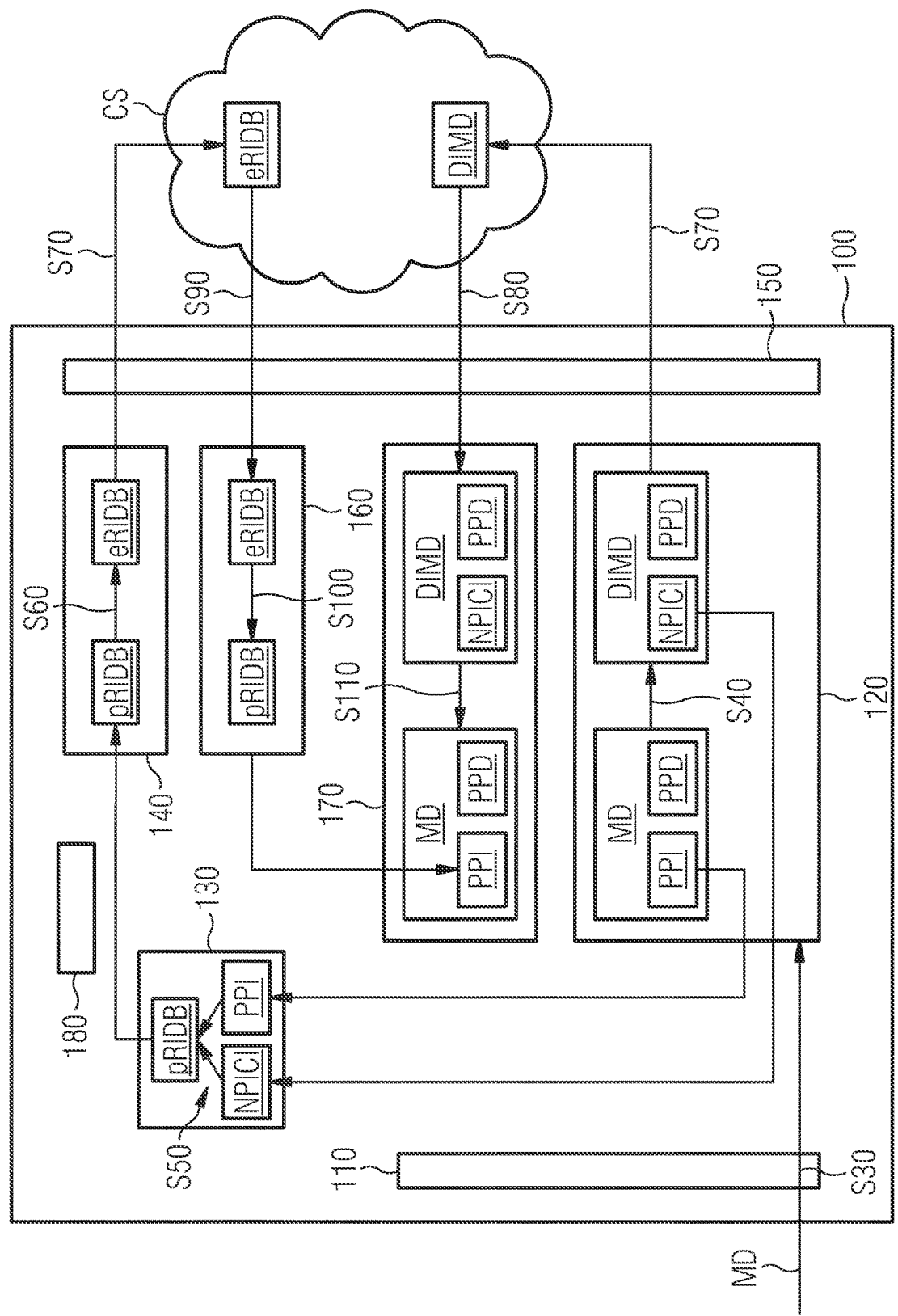
Figure 4:
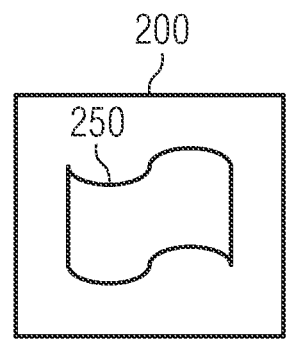
Figure 5:
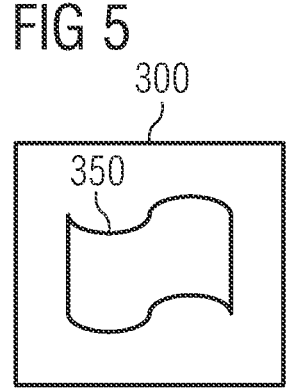

In the drawings:

FIG. 1 shows a schematic flow diagram illustrating a method according to the first aspect of the present invention;

FIG. 2 shows a schematic block diagram illustrating a system according to the third aspect of the present invention, and further illustrating the method according to FIG. 1, a method according to an embodiment of the fourth aspect of the present invention as well as a system according to the sixth aspect of the present invention;

FIG. 3 shows a schematic block diagram illustrating options and variants for the methods of FIG. 1 and FIG. 2, as well as a gateway according to an embodiment of the second aspect of the present invention and a gateway according to an embodiment of the fifth aspect of the present invention;

FIG. 4 shows a schematic block diagram illustrating a computer program product according to an embodiment of the seventh aspect; and FIG. 5 shows a schematic block diagram illustrating a data storage medium according to an embodiment of the eighth aspect.

Although specific embodiments have been illustrated and described herein, it will be appreciated by those of ordinary skill in the art that the variety of alternate and/or equivalent implementations may be substituted for the specific embodiments shown and described without departing from the scope of the present invention. Generally, this application is intended to cover any adaptations or variations of the specific embodiments discussed herein.

DETAILED DESCRIPTION OF THE INVENTION

FIG. 1 shows a schematic flow diagram illustrating a method according to the first aspect of the present invention, i.e. a computer-implemented method for securely storing medical data, MD. It is also referred to the following FIG. 2 and FIG. 3 for easier understanding of the steps of the method.

FIG. 2 shows a schematic block diagram illustrating a system 1000 according to the third aspect of the present invention, a gateway 100 according to the second aspect of the present invention as well as further illustrating the method according to FIG. 1. Further, FIG. 2 serves to illustrate a method according to an embodiment of the fourth aspect of the invention, a gateway 100 according to an embodiment of the fifth aspect of the invention, and a system 1000 according to an embodiment of the sixth aspect of the invention.

FIG. 3 shows a schematic block diagram illustrating method steps for securely storing (and optionally retrieving) backed-up medical data on/from a cloud storage CS according to the method of FIG. 1 in more detail. In addition, FIG. 3 shows a schematic block diagram of a gateway 100 according to an embodiment of the second aspect of the present invention which will be described subsequently.

Further, FIG. 3 shows a schematic block diagram illustrating method steps of retrieving backed-up medical data from a cloud storage CS of a method according to an embodiment of the fourth aspect of the present invention, and a gateway 100 according to an embodiment of the fifth aspect of the present invention.

Although some method steps are described together with parts or modules of the gateway 100, it should be understood that the method steps may also be performed by other entities, systems, or devise. Similarly, the gateway 100 will usually perform various other functions apart from the ones described herein.

In a step S10, which is not an essential part of the invention, medical data, MD, are acquired by medical data sources 1. In the present context, it is assumed that the medical data sources 1 are present on the premises of a hospital (tenant) and are connected to a secure environment SE i.e. to a secure network. However, medical data sources 1 may also be located off the premises and may enter the secure environment SE by other means. For example, a patient may upload, or bring, their previous medical history to the hospital, a physician previously treating a patient may transmit medical data collected from said patient, and so on.

As illustrated in FIG. 2, such medical data sources 1 may comprise medical imaging scanners (such as magnetic resonance imaging, MRI, scanners, computed tomography, CT, scanners, X-ray scanners, ultrasound devices and so on), a fluoroscopy station, patient assessments by a physician which are then digitized using a user interface, patient monitoring data such as from a heart rate monitor, a respiration monitor, camera pictures from surgically inserted cameras, data from implanted transmitting devices and/or the like.

In a step S20, the acquired data may be persisted within the secure environment SE. In the case of imaging data (as one example for medical data), they may be persisted for example in a picture archiving and communication system, PACS 10, of the secure environment SE. The data may be stored by the PACS 10 in the well-known DICOM format.

After it is persisted in the PACS 10, the acquired data or the fact of the availability at the PACS 10 may be transmitted to a list of subscribers. The subscribers may be devices, monitoring stations, software modules for analysis or any other post-processing or reporting system.

In the present example, the data are also transmitted, in a step S30, to a gateway 100, which may also be designated as a "medical data gateway", MDG. One example for such a medical data gateway is the Teamplay (registered trademark) receiver by Siemens Healthineers. Such a gateway will not only fulfil the usual functions of gateways (such as providing interoperability between networks, protocol translations and so on) but will also, as will be described in the following in the context of FIG. 3, implement various software modules. As such, the gateway 100 may be realized as, or as comprising, a computing device including in particular a processing unit (CPU), a working memory (RAM), a data storage unit (persistent memory), as well as at least one input and at least one output interface, wherein the components of the computing device are operatively coupled to one another.

In the step S30, also other medical data MD not stemming from the PACS 10 may be transmitted to the gateway 100, in particular medical data, MD, not related to medical imaging. Such data may include monitoring data (heart rate, respiration rate, EEG data, . . . ), data input by a physician into a user interface (e.g. at a personal computer, PC). However, also medical imaging data may be transmitted to the gateway 100 by other ways than via the PACS 10.

As result of any combination of steps S10 to S30, medical data MD are acquired (or: obtained) within the secure environment SE. The acquired, or obtained, medical data MD comprise, or consist of, patient identifier data PID and patient property data, PPD.

In a step S40, de-identified medical data DIMD are generated within the secure environment SE, in particular by the gateway 100. The de-identified medical data DIMD are generated by replacing the patient identifier data PID in the medical data, MD, with respective non-patient-identifying coded identifiers, NPICI, as is illustrated also in FIG. 3. For example, each non-patient-identifying coded identifier NPICI may be a hash key of the patient identifier data PID, of parts of the patient identifier data PID, and/or may be based on at least parts of the patient identifier data PID and other data.

Additionally, in a step S50, a re-identifying database, RIDB, is generated within the secure environment SE, in particular by the gateway 100. The re-identifying database, RIDB, indicates (preferably one-on-one) correspondences between the non-patient-identifying coded identifier NPICI and the patient identifier data, PID, see for example FIG. 3. For example, the re-identifying database, RIDB, may comprise, or consist of, a table with all data fields of the patient identifier data PID for each patient, and in addition with a data field indicating the non-patient-identifying coded identifier NPICI corresponding to each patient. Within the secure environment SE, specifically the gateway 100, the re-identifying database RIDB may be present in a plain text state which may be designated as pRIDB.

Since the re-identifying database, RIDB, has not only the function of providing the (preferably one-on-one) correspondences but also the function of providing the parts of the medical data, MD, missing from the de-identified medical data DIMD it is preferred that the re-identifying database, RIDB, comprises the complete patient identifier data, PID.

Step S50 is advantageously performed simultaneously or concurrently with step S40.

In a step S60, an encrypted re-identifying database, eRIDB, is generated in the secure environment SE by applying at least one symmetric and/or asymmetric encryption method (or: encryption protocol) to the re-identifying database, RIDB. The encryption protocols may be applied by a hardware security module, HSM, which may be part of the gateway 100.

In the present example, both a symmetric encryption protocol and an asymmetric encryption protocol are applied, first the symmetric encryption protocol then the asymmetric encryption protocol. However, it shall be understood that different protocols, different orders of their application, different numbers of encryption protocols and so on may be applied. The inventors have found that the presently described example provides a good balance between security and feasibility, since more, and more secure, encryption protocols increase the required time for applying them as well as the necessary computational power.

Moreover, in the present example, the 256-bit advanced encryption standard, AES256, is used as the symmetric encryption protocol, and RSA (for example 2048 bit RSA or 4096 bit RSA) is used as the asymmetric encryption protocol. It shall be understood that any other suitable encryption method or standard may be equally or additionally applied. For example, AES256 may be replaced by elliptic curve cryptography, ECC.

If the re-identifying database, RIDB, is designated with the symbol $M_{rd}$, then the encrypting S60 may be performed in the following sub-steps:

In a step S61, AES256 encryption $f_{enc,AES}$ is performed on $M_{rd}$:

$$C_{rd} = f_{enc,AES}(M_{rd}, K),$$

wherein $C_{rd}$ is the cipher text and K is a random key.

Then, in a step S62, a public key, PUK, and a private key, PRK, for the RSA protocol are generated in any of the commonly known ways. For example, two large, not too close primes p and q are selected and multiplied, p*q=n. Carmichael's (or, alternatively, Euler's) totient function $\phi(n)$ is calculated, and an integer e is chosen such that $1<e<\phi(n)$ and with e and $\phi(n)$ coprime, i.e. $\gcd(e, \phi(n))=1$, gcd designating the greatest common divisor. Then, an integer d is determined as $d=e^{-1} \mod(\phi(n))$, i.e. d is the modular multiplicative inverse of e module $\phi(n)$.

Thus, the RSA public key, PUK, is given by $\{e, n\}$ and the RSA private key, PRK, is given by $\{d, n\}$.

In a step S63, using the public key, PUK, the cipher $C_{rd}$ is further encrypted to $C'_{rd} = f_e(C_{rd}) = C_{rd}^e \pmod{\phi(n)}$. Thus, $C'_{rd}$ corresponds to the encrypted re-identifying database, eRIDB, when Mrd is set to be the re-identifying database, RIDB.

In order to protect the public key, PUK, also inside the secure environment SE, the public key, PUK, may be stored in an encrypted state (ePUK) at the secure environment SE, wherein for this encryption a secure-environment-specific token, SEST, of the secure environment SE is used.

For example, a public key encryption $f_{PUK}$ may be applied, given by $$f_{PUK}(PUK) = PUK + SEST,$$

wherein the addition here may be an addition modulo $\phi(n)$.

The secure-environment-specific token, SEST, may be generated in any of a number of ways using codes or numbers available at the secure environment SE. For example, the secure-environment-specific token, SEST, may comprise, or be based on, any or all of:

an identifier token of the secure environment SE;
an identifier token of at least one device in the secure environment SE (for example of the gateway 100;
a version number of the re-identifying database, RIDE, to be encrypted;
a serial number of at least one medical data source 1;
an RFID code of a dongle owned by an administrator;
and/or the like.

Similarly, the private key, PRK, may also be stored in an encrypted state (ePRK) at the secure environment SE. For example, a private key encryption function, $f_{PRK}$ may be applied, with $$f_{PRK}(PRK)=PRK+H_{MSK},$$

wherein $H_{MSK}$ designates a master key which may be owned, for example, by a hospital administrator. The master key $H_{MSK}$ in turn may be stored in an encrypted state generated using a master key encryption function $f_{MSK}$, for example:

$$f_{MSK}(H_{MSK})=H_{MSX}+SEST.$$

If $RDBV_{DEK}$ is the re-identification database, RIDB, encryption key, then it may be stored in an encrypted state as $$f_{encr}(RDBV_{DEK})=RDBV_{DEK}+PUK.$$

In a step S70, the encrypted re-identifying database, eRIDB, as well as the de-identified medical data DIMD are then stored on a cloud storage, CS, outside of the secure environment SE. Preferably, data in transit are encrypted using TLS v1.2 (or higher) with strong ciphers enforced.

As an optional step, also the de-identified medical data DIMD may be encrypted to provide encrypted de-identified medical data eDIMD which may then be stored on the cloud storage CS. In this case, preferably no plain text de-identified medical data, pDIMD, is stored on the cloud storage CS. The encryption protocols and/or keys used therein may be the same as for the encrypted re-identifying database eRIDB but are preferably different.

However, storing plain text de-identified medical data, pDIMD, on the cloud storage has the advantage that they can be provided S200 to different processes by the cloud storage CS without any sensitive patient identifier data, PID being leaked. In this way, for example, the plain text de-identified medical data, pDIMD, may be made available (i.e. transmitted or allowed to be retrieved) for the purpose of training an artificial intelligence entity such as an artificial neural network. The plain text de-identified medical data, pDIMD, may thus be used as, or as basis for, training data including ground truth labels.

In some variants, the encrypted re-identifying database eRIDB and/or the de-identified medical data DIMD (either as eDIMD or pDIMD) may also be stored in other places apart from the cloud storage CS. For example, additional backup copies of both or either can be stored in the gateway 100, in any of the medical data sources 1, in the PACS 10 and/or the like. For example, the encrypted re-identifying database eRIDB and/or the de-identified medical data DIMD could be encapsulated in the DICOM format and deposited into the PACS 10.

Several variants of the encrypting step S60 are possible. For example, it need not be the humanly readable (plain text), entire re-identifying database, pRIDB, to which the encryption protocols are applied. Instead, in some variants, the re-identifying database, RIDB, may first be divided up into several chunks, for example a fixed number of chunks, or into chunks of fixed sizes.

One option for this is to distribute the bits of the re-identifying database, RIDB, into a matrix structure, and then encrypt each cell of the matrix structure individually using the above described steps S61-S63. For example, a matrix structure of 10×10 cells may be used, wherein a first bit (or a larger portion) is put into the first cell, a second bit (or portion) is put into the second cell, and so on until the 100th bit(or portion) is put into the 100th cell, then the 101st bit (or portion) is again put into the first cell and so on. In other words, bit (or portion) number x is put into the cell number x mod 100. Other ways of splitting of the re-identifying database RIDB can be readily envisaged as well.

In other words, in the above formulae, the symbol $M_{rd}$ may not designate the entire re-identifying database RIDB but each individual chunk of the re-identifying database RIDB separately. This means that for decrypting the re-identifying database RIDB all of the (encrypted) chunks must be acquired, and the decrypted chunks must then be arranged in the correct order according to the matrix structure such as to re-construct the original re-identifying database RIDB.

Storing S70 the encrypted re-identifying database eRIDB on the cloud storage CS then in these variants comprises storing each encrypted chunk on the cloud storage CS.

Advantageously, the encrypted chunks themselves do not indicate to which cell of the matrix structure they belong. Instead, they may comprise a coded cell identifier (e.g. a hash value) which is used to uniquely identify the chunk.

Then, a chunk correspondence list, CCL, may be generated which indicates which coded cell identifier indicates correspondence to which cell of the matrix structure so that the decrypted chunks can be re-arranged again in the matrix structure so as to yield the readable re-identifying database RIDB.

Even stronger security can be achieved when it is taken into account that usually it is desired to prepare and maintain backups according to at least two versions. It is evident that, if one were to only ever store a single backup on the cloud storage CS, wherein the currently present backup is overwritten during the upload of the next backup, then some mishap or error during the upload may result in a situation in which no valid backup at all is present. Therefore, it is desirable that at least two differently versioned backups of all files or data to be backed up are present on the cloud storage CS at all times.

If now the re-identifying database RIDB as one such file to be backed up is divided into chunks which are then encrypted and which are then stored in step S70 on the cloud storage CS then the entirety of the encrypted chunks represents the encrypted re-identifying database eRIDB. For example, this may be one hundred chunks. If two versions, e.g. from two different time points, of the re-identifying database RIDB are backed up, this means that there will be two hundred chunks representing two different encrypted re-identifying databases eRIDB on the cloud storage CS at all times.

If an attacker were to gain access to the cloud storage CS, the attacker would find (in this simple example) two hundred encrypted chunks which are only identified by the coded cell identifiers, e.g. hash values. Thus, the attacker will not only not know how many chunks represent one encrypted re-identifying database eRIDB—the attacker will also not know which chunks belong to which version. However, due to the way the re-identifying database, RIDB, is split up before the encoding, plain text (i.e. a readable re-identifying database RIDB) is only obtainable when the decrypted chunks are arranged in the correct order.

So, for each try that the attacker makes to decrypt a number of chunks, the attacker must then also try a large number of different orders in which to arrange the chunks to find out whether the decryption has been successful. For example, there are 100! ways to arrange one hundred chunks in a ten by ten matrix.

Security is further increased by using different encryption keys for the asymmetric encryption protocol and/or symmetric encryption protocol for each version of the re-identifying database RIDB.

A version correspondence list, VCL, indicating which encrypted chunks on the cloud storage CS belong to which version and to which cell therein may be generated so that the administrators of the secure environment SE are able to retrieve the re-identifying database RIDB from the encrypted chunks representing the encrypted re-identifying database eRIDB.

The VCL may be encrypted in any suitable way to form an encrypted version correspondence list, eVCL, e.g. again according to steps S61-S63, either using the same keys or, preferably, different keys. Accordingly, an attacker would first have to know of this arrangement, and then to decrypt the version correspondence list, VCL, first, in order to know which chunks must be decrypted using the same decryption protocols, before decryption of said chunks can be started.

The method may also be augmented to a secure data storage and retrieval method as will be briefly described in the following in particular with respect to FIG. 3.

In a step S80, the de-identified medical data DIMD (either encrypted, eDIMD, or plain text, pDIMD) are retrieved from the cloud storage CS into the secure environment SE, in particular by (and into) the gateway 100. In case of eDIMD stored on the cloud storage CS, the retrieving S80 comprises downloading the eDIMD and applying a decryption step on the eDIMD to yield the pDIMD. In case of pDIMD stored on the cloud storage CS, the pDIMD are simply downloaded to perform the retrieving S80.

In a step S90, the encrypted re-identifying database eRIDB is retrieved (specifically: downloaded) from the cloud storage CS into the secure environment SE, in particular by (and into) the gateway 100. Depending on the variant used, retrieving the encrypted re-identifying database eRIDB may comprise downloading a single file, or a number of encrypted chunks, optionally together with a version correspondence list VCL (preferably an encoded version correspondence list eVCL).

In a step S100, the encrypted re-identifying database eRIDB is decrypted (the specifics again depending on which kind of encryption has been used) in the secure environment SE in order to obtain the (plain text) re-identifying database, RIDB (which may also be designated as pRIDB). In some of the variants described in the foregoing, the decrypting may be applied to each of a number of chunks representing the encrypted re-identifying database eRIDB, followed by regenerating the plain text re-identifying database pRIDB by undoing the distribution into the chunks according to (for example) the matrix scheme.

In a step S110, the medical data, MD, are re-generated from the DIMD by replacing the non-patient-identifying coded identifiers NPICI with the corresponding patient identifier data PID based on the one-to-one correspondence indicated by the (decrypted, i.e. now plain text) re-identifying database RIDB. This step is also illustrated in FIG. 3.

In other words, the pseudonymized non-patient-identifying coded identifiers NPICI are remapped to the original patient identifier data PID. In order to emphasize and clarify that the medical data, MD, are present within the gateway 100 in a plain text version, they may also be designated as pMD.

Referring back to FIG. 2, the method may further comprise a step S200 of providing the de-identified medical data DIMD (in particular pDIMD), from the cloud storage CS to a processing entity 3Pout outside of the secure environment SE. For example, in a step S210, the processing entity 3Pout may utilize the de-identified medical data, DIMD for training an artificial intelligence entity, for example for machine learning, preferably an artificial neural network or the like.

If a processing entity 3Pin inside of the secure environment SE requests the medical data MD either the de-identified medical data DIMD or even the medical data MD (including the patient identifier data PID) may be provided, depending on the desired level of security, the clearance of the processing entity 3Pin, and so on. The processing entities 3Pout, 3Pin may access the de-identified medical data DIMD for example via a web browser.

FIG. 3 also illustrates the gateway 100 according to an embodiment of the second aspect of the present invention as well as a gateway 100 according to an embodiment of the fifth aspect of the present invention. The gateway 100 may in particular be configured to perform at least steps S30-S70 of the method of FIG. 1 and FIG. 2, and preferably also steps S80-S110.

Specifically, the gateway 100 may comprise:
an input module 110 configured to obtain S30 medical data MD which include patient property data PPD as well as patient identifier data PID, wherein the patient identifier data PID indicate at least one patient to which the patient property data PPD correspond;
a de-identifying module 120 configured to generate S40 de-identified medical data DIMD by replacing the patient identifier data PID in the medical data MD with non-patient-identifying coded identifiers NPICI;
a database generating module 130 configured to generate S50 a re-identifying database RIDB (in plain text, i.e. pRIDB) indicating one-on-one correspondences between the non-patient-identifying coded identifiers NPICI and the patent identifier data PID;
an encryption module 140 configured to generate S60 an encrypted re-identifying database eRIDB by applying at least one symmetric and/or asymmetric encryption method to the (plain text) re-identifying database pRIDB;
a communication module 150 configured to transmit S70 the encrypted re-identifying database eRIDB and the de-identified medical data DMID to be stored on a cloud storage CS off the secure environment SE.

The input module 110 may be part of, or be realized as, an internal communication module (or: internal communication interface) which is configured for data transmission and reception within the secure environment SE. The communication module 150 may in that case be designated as an external communication module 150, or as an external communication interface.

It shall be understood that the communication module 150 may further be configured to retrieve S80, S90 the DIMD (pDIMD or eDIMD) and the encrypted re-identifying database eRIDB from the cloud storage CS.

The gateway 100 may further comprise a decryption module 160 for decrypting S100 the encrypted re-identifying database eRIDB (and optionally the eDIMD). The encryption module 140 and the decryption module 160 may be integrated into one another, or be realized as separate, or may have overlapping components. For example, for some encryption/decryption protocols, decryption and encryption comprise, or consist of, the same operation. As is also true for any other module, in particular the encryption module 140 and/or the decryption module 160 may be realized as hardware and/or as software. Therefore, for example, for an operation that is the same for encryption as well as decryption, a corresponding module or sub-module may be realized as hardware.

The gateway 100 may further comprise a re-identifying module 170 configured to re-generate S110 the medical data MD from the de-identified medical data DIMD by replacing (or associating) the non-patient-identifying coded identifier NPICI in the de-identified medical data DIMD with the corresponding patient identifier data PID based on the (plain text) re-identifying database pRIDB obtained from the decryption module 160. Thus, the gateway 100 may be configured to not only perform any embodiment of the method for securely storing medical data MD but may also be configured to securely retrieve the stored medical data MD from the cloud storage CS.

The entire function of the gateway 100 may be controlled by a controller module 180 (e.g. a microcontroller executing a corresponding computer program with executable computer program instructions) of the gateway 100.

FIG. 2 also illustrates a system 1000 according to an embodiment of the third aspect of the present invention and/or of an embodiment of the sixth aspect of the present invention. The system 1000 may comprise the gateway 100 and the cloud storage CS which are operatively linked to one another so that the system 1000 is configured to perform, or allow performing, the method according to any embodiment of the first aspect of the present invention. The system 1000 may optionally comprise any number of medical data sources 1, a PACS 10 and/or the like, and may even comprise the secure environment SE.

FIG. 4 shows a schematic block diagram illustrating a computer program product 200 according to an embodiment of the seventh aspect, the computer program product 200 comprising executable program instructions 250 configured to, when executed, perform the method according to any embodiment of the first aspect and/or the method according to any embodiment of the fourth aspect of the present invention.

FIG. 5 shows a schematic block diagram illustrating a non-transient computer-readable data storage medium 300 according to an embodiment of the eighth aspect, comprising executable program instructions 350 configured to, when executed, perform the method according to any embodiment of the first aspect and/or the method according to any embodiment of the fourth aspect of the present invention.

In the foregoing detailed description, various features are grouped together in one or more examples or examples with the purpose of streamlining the disclosure. It is to be understood that the above description is intended to be illustrative, and not restrictive. It is intended to cover all alternatives, modifications and equivalents. Many other examples will be apparent to one skilled in the art upon reviewing the above specification. In particular, the embodiments and configurations described for the system and gateway can be applied accordingly to the method according to the invention, and vice versa.

The embodiments were chosen and described in order to best explain the principles of the invention and its practical applications, to thereby enable others skilled in the art to best utilize the invention and various embodiments with various modifications as are suited to the particular use contemplated. In the appended claims and throughout the specification, the terms "including" and "in which" are used as the plain-English equivalents of the respective terms "comprising" and "wherein," respectively. Furthermore, "a" or "one" does not exclude a plurality in the present case.

When data are mentioned it shall be understood that this may include plain text or encrypted data, unless it is otherwise explicitly or implicitly evident from the context.

The invention claimed is:

1. A computer-implemented method for securely storing medical data comprising at least steps of:
obtaining, in a secure environment, medical data which include patient property data as well as patient identifier data wherein the patient identifier data indicate at least one patient to which the patient property data correspond;
generating, in the secure environment de-identified medical data by replacing the patient identifier data in the medical data, with respective non-patient-identifying coded identifiers, wherein each non-patient-identifying coded identifier is a hash key of the patient identifier data PID, of parts of the patient identifier data PID, and/or is based on at least parts of the patient identifier data PID and other data;
generating, in the secure environment, a re-identifying database indicating correspondences between the non-patient-identifying coded identifiers and the patient identifier data;
generating an encrypted re-identifying database by applying, in the secure environment, at least one asymmetric encryption method to the re-identifying database, wherein at least an asymmetric encryption method is applied when generating the encrypted re-identifying database, the asymmetric encryption method being based on a private key and a public key wherein a public key of the asymmetric encryption method is used for the asymmetric encryption and wherein a private key for a corresponding decryption remains in the secure environment;
storing the encrypted re-identifying database and the de-identified medical data on a cloud storage outside of the secure environment.

2. The method of claim 1, wherein the public key and/or the private key are stored in a domain of the secure environment in a respective encrypted state/wherein the corresponding encrypted state results from encrypting the public key, or the private key respectively, using a secure-environment-specific token.

3. The method of claim 2, wherein the secure-environment-specific token is based on at least one of:
an identifier token of the secure environment;
an identifier token of at least one device in the secure environment;
an identifier token of at least one software application used within the secure environment and/or
a version number of data to be encrypted using the public key.

4. The method of claim 1, wherein the encrypted re-identifying database is additionally stored in a device in the secure environment.

5. The method of claim 1, wherein the encrypted re-identifying database is generated as consisting of, or processed to consist of, a plurality of chunks which are stored on the cloud storage.

6. The method of claim 5, wherein chunks belonging to at least two different versions of the re-identifying database are stored in an encrypted state on the cloud storage; and wherein the method also comprises a step of generating a version correspondence list, indicating which chunks belong to which version, whereas the chunks do preferably not contain any plain text information about a version to which they belong.

7. The method of claim 6, comprising further steps of encrypting the version correspondence list to obtain an encrypted version correspondence list, and of storing the encrypted version correspondence list on the cloud storage.

8. The method of claim 1, comprising a step of generating encrypted de-identified medical data, wherein storing the de-identified medical data on the cloud storage comprises, or consists of, storing the encrypted de-identified medical data on the cloud storage.

9. The method of claim 1, comprising a step of retrieving the medical data from the cloud storage comprising:

retrieving the de-identified medical data from the cloud storage;

retrieving the encrypted re-identifying database from the cloud storage;

decrypting, in the secure environment the encrypted re-identifying database in order to obtain the re-identifying database;

regenerating the medical data from the de-identified medical data by replacing, or associating, the non-patient-identifying coded identifiers in the de-identified medical data with the corresponding patient identifier data based on the re-identifying database.

10. The method of claim 1, comprising a step of providing the de-identified medical data from the cloud storage to a processing entity outside of the secure environment.

11. The method of claim 10, comprising training, by the processing entity, an artificial intelligence entity based on the de-identified medical data.

12. A non-transitory, computer-readable data storage medium comprising executable program instructions configured to, when executed, perform the method according to claim 1.

13. A gateway for use in a secure environment, comprising:

an input module configured to obtain medical data which include patient property data as well as patient identifier data wherein the patient identifier data indicate at least one patient to which the patient property data correspond;

a de-identifying module configured to generate de-identified medical data by replacing the patient identifier data in the medical data with respective non-patient-identifying coded identifiers, wherein each non-patient-identifying coded identifier is a hash key of the patient identifier data PID, of parts of the patient identifier data PID, and/or is based on at least parts of the patient identifier data PID and other data;

a database generating module configured to generate a re-identifying database indicating correspondences between the non-patient-identifying coded identifiers and the patent identifier data;

an encryption module configured to generate an encrypted re-identifying database by applying at least one asymmetric encryption method to the re-identifying database, wherein at least an asymmetric encryption method is applied when generating the encrypted re-identifying database, the asymmetric encryption method being based on a private key and a public key wherein a public key of the asymmetric encryption method is used for the asymmetric encryption and wherein a private key for a corresponding decryption remains in the secure environment;

a communication module configured to transmit the encrypted re-identifying database and the de-identified medical data to be stored on a cloud storage outside of the secure environment.

* * * * *